United States Patent [19]

Yamada et al.

[11] Patent Number: 5,135,858
[45] Date of Patent: Aug. 4, 1992

[54] PROCESS FOR BIOLOGICAL PRODUCTION OF ORGANIC ACIDS

[75] Inventors: Hideaki Yamada, 19-1, Matsugasaki-Kinomoto-Cho, Sakyo-Ku, Kyoto-Shi, Kyoto-Fu; Toru Nagasawa, Kyoto; Tetsuji Nakamura, Yokohama, all of Japan

[73] Assignees: Hideaki Yamada; Nitto Kagaku Kogyo Kabushiki Kaisha, both of Tokyo, Japan

[21] Appl. No.: 659,878

[22] Filed: Feb. 22, 1991

[30] Foreign Application Priority Data

Feb. 28, 1990 [JP] Japan .................... 2-48134

[51] Int. Cl.$^5$ .................... C12P 13/04; C12P 17/00; C12P 13/00; C12R 1/01
[52] U.S. Cl. .................... 435/106; 435/110; 435/117; 435/120; 435/121; 435/122; 435/128; 435/129; 435/136; 435/142; 435/822
[58] Field of Search ............... 435/106, 117, 227, 128, 435/120, 121, 122, 129, 110, 136, 142, 822

[56] References Cited

U.S. PATENT DOCUMENTS

| | | | |
|---|---|---|---|
| 4,629,700 | 12/1986 | Prevatt et al. | 435/128 |
| 4,637,982 | 1/1987 | Yamada et al. | 435/227 |
| 4,705,752 | 11/1987 | Boesten et al. | 435/106 |
| 4,900,672 | 2/1990 | Yamada et al. | 435/227 |

FOREIGN PATENT DOCUMENTS 8607386 12/1986 PCT Int'l Appl. ............... 435/227

OTHER PUBLICATIONS

Biotech Abs. 88-12666 Kobayashi et al EJABDD "Appl. Microbio Biotech" (1988) 29, 2-3 231-33.
Biotech Abs 89-09162 Nagasawa et al TRBIDM Trends Biotech (1989) 7, 6, 153-8.
Biotech Abs 90-07776 J. Chem Soc. Chem Commun (1990) 8 648-50.
Biotech Abs 91-01772 Teleay "Tetrahed Letters"(1990) 31, 49 7223-26 Cohen et al.
Biotech Abs 86-06566 Novo EP-178106 Apr. 1986.
JPOABS 61-282089 Dec. 1986.
JPOABS 01-171478 (Jul. 1989) Kawakami Abs Pub Oct. 6, 1989.
Biotech 91-04638 Nagasawa et al. EJABDD (1990) 34, 3, 322-24 Applied Micro Biotech).
Derwent 91-02254 Agency J02249491 May 1990.
JPOABS 61-162191 Jul. 1986 Publ Abs Dec. 6, 1986 Nitto Chem.
JPOABS 61-40795 Feb. 1986 Pub Abs Jul. 11, 1986 Asahi.

*Primary Examiner*—Herbert J. Lilling
*Attorney, Agent, or Firm*—Emmanuel J. Lobato; Robert E. Burns

[57] ABSTRACT

An improved biological conversion of a nitrile such as acrylonitrile or a cyanopyridine into the corresponding carboxylic acid such as acrylic acid or a nicotinic acid by the action upon the nitrile of a nitrilase enzyme, in which the improvement resides in the use as the source of the enzyme of a microorganism of Rhodococcus, such as *Rh. rhodochrous* J-1, FERM BP-1478, which is cultured in the presence of a lactam compound.

15 Claims, No Drawings

PROCESS FOR BIOLOGICAL PRODUCTION OF ORGANIC ACIDS

BACKGROUND OF THE INVENTION

1. Field of the Art

The present invention relates to production of organic acids by a biological technique. More particularly, the present invention relates to conversion of nitrile compounds into the corresponding organic or carboxylic acids by the action of microorganisms.

Organic or carboxylic acids are utilized as materials for producing various chemicals, and it is known that acrylic acid and methacrylic acid, in particular, are important as materials for, e.g. polymeric products and nicotinic acid is important for use in medicines.

2. Related Art and the Problems Inherent Therein

Known in the art for converting nitrile compounds into the corresponding acids are chemical synthesis technique and biological technique. The chemical synthesis may entail the problem of disposal of wastes resulting from the synthesis in which a strong mineral acid is used for hydrolyzing the nitrile. The biological technique, on the other hand, is advantageous in that an enzyme inherent in microorganism is used as the hydrolysis catalyst whereby the acid is obtainable under mild conditions.

Examples of the biological technique may include those where use is made as the microorganism of Bacillus, Bacteridium, Micrococcus, and Brevibacterium as set forth in U.S. Pat. No. 3,940,316, of Acinetobacter as set forth in Japanese Patent Publication No. 2596/1988, of Corynebacterium as set forth in Japanese Patent Publication No. 56800/1988, and of Alcaligenes as set forth in Japanese Patent Laid-Open Publication No. 132392/1989.

The first group of microorganisms as set forth in U.S. Pat. No. 3,940,316 do not appear to us to be equipped with high activity so that the process can be held practical.

In view of this, an improvement has been produced, in e.g. Japanese Patent Publication No. 2596/1988, loc. cit, to enhance the catalyst activity of the microorganisms, which comprises culturing a microbial strain in the presence of a nitrile compound added as an inducer of the hydrolysis enzyme. This improvement may, however, entail a problem such that the microorganism utilizes the nitrile compound added to the culture medium during the culturing and it is required to supplement the nitrile consumed whereby it may be difficult to maintain the microorganism at the highest activity level possible when the operation is conducted in a commercial scale. It may be another problem that the activity so obtained is not very satisfactory.

SUMMARY OF THE INVENTION

It has now been found that culturing a microbial strain belonging to Rhodococcus in a culture medium having a lactam compound added thereto easily produces cells capable of strongly producing a nitrilase enzyme, which enzyme can be used on a commercial scale as a catalyst for converting a nitrile compound into a corresponding acid.

The present invention thus presents an improved process in a process for producing organic acids which comprises converting a nitrile compound by the action thereon of a nitrilase enzyme inherent in a microorganism into the corresponding organic acid, which improved process comprises the use as the catalyst of an enzyme which is obtained by culturing a microbial strain of Rhodococcus in the presence of a lactam compound.

In accordance with the present invention, a nitrilase activity is induced by culturing a microbial strain belonging to in a culture medium to which a lactam compound has been added. During the culturing, the lactam compound in the culture medium is little utilized by the microorganism whereby it remains in the culture medium in a given level of concentration, whereby the induction of the nitrilase enzyme takes place steadily resulting in easy production of microbial cells having highly active nitrilase activity.

DESCRIPTION OF THE PREFERRED EMBODIMENT

Introduction of nitrilase enzyme

The microorganisms which are used in the present invention as sources of nitrilase enzymes are those which belong to Rhodococcus, and examples of the microorganisms include *Rhodococcus rhodochrous* ATCC 33278, Rhodococcus sp. NCIB 11215, Rhodococcus sp. NCIB 11216, and *Rhodococcus rhodochrous* J-1, FERM BP-1478.

The preferable microorganism is *Rhodococcus rhodochrous* J-1, FERM BP-1478, which was deposited at Fermentation Research Institute, Agency of Industrial Sciences and Technology, Japan as an international deposit under the Budapest Treaty on the International Recognition of the Deposit of Microorganisms for the Purpose of Patent Procedure, whose bacteriological properties are disclosed in European Patent Publication No. 0307926.

These microorganisms are used in accordance with the present invention after being cultured in a culture medium having a lactam compound added. Any culture media are used provided that the microorganisms of Rhodococcus will grow thereon in the presence of a lactam compound added. For example, culture media which contain, as the carbon source, glucose, sucrose or glycerol; as a nitrogen source, peptone, a meat extract, a yeast extract, an amino acid or various inorganic or organic ammonium salt; and other optional ingredients such as an inorganic salt, a metal salt in a very small amount, a vitamin, and the like; and a lactam compound.

Any lactam compounds can be used provided that they are organic cyclic compounds having a structure —CONH— in the ring, namely a cyclic amides. Preferred examples of lactams include intramolecular amides of $\omega$-amino acids of 4 to 6 carbon atoms, and more preferred examples include $\gamma$-butyrolactam, $\delta$-valerolactam and $\epsilon$-caprolactam. These lactam compounds can be used in admixture.

The amount of lactams for addition to culture media may be 0.05 to 2.0(w/v) %, preferably 0.1 to 1.0(w/v) %.

Culturing may be carried out at the pH of the media of 6 to 10, preferably 7 to 9, at a temperature of 15° to 37° C., preferably 25° to 30° C. for 1 to 7 days under aerobic conditions.

Hydrolysis of nitriles

The biological production of organic acids in accordance with the present invention comprises converting nitrile compounds into the corresponding acids (—CN- →—COOH) by the action thereupon of a nitrilase enzyme inherent in a microorganism of Rhodococcus. The expression "by the action thereupon of a nitrilase enzyme inherent in a microorganism" herein used includes any types of the enzymes and any modes of action of the enzymes upon their substrates, i.e. nitriles, provided that the enzymes are those produced by microorganisms and that the enzymes are capable of converting their substrates which are nitriles into the corresponding organic acids. For instance, included in the present invention are methods where a culture liquor of a microorganism grown therein as shown herein above or a suspension of the cells obtained from the culture liquor by filtration is added a nitrile compound which is a substrate for the enzyme; where a cell derivative such as crushed cells, or crude or purified enzyme produced therefrom or immobilized cells or cell derivative in suspension is added a nitrile compound which is a substrate for the enzyme; and where the culturing of a microbial strain in the presence of a lactam compound is conducted in the presence of a nitrile compound whereby the induction of the enzyme and the action of the enzyme upon the nitrile compound proceed in situ.

No restriction may be imposed onto the substrate concentration in the reaction solution, but the range of 0.1 to 10 (w/v) % is preferable. The substrate can be added to the reaction solution as a lump or portion-wise.

The temperature and the pH for the hydrolysis reaction may be 5° to 50° C. and pH 4 to 10, respectively. The reaction time which may depend on the substrate concentration used, the cell concentration used or other reaction conditions used may be 1 minute to 48 hours.

Examples of the nitrile compounds to be hydrolyzed in accordance with the present invention include aliphatic and aromatic mononitriles and dinitriles. The aliphatic nitriles are preferably those of 2 to 6 carbon atoms, and include unsaturated nitriles such as acrylonitrile, methacrylonitrile and crotononitrile; saturated nitriles such as acetonitrile, propionitrile, butyronitrile, and valeronitrile; and dinitriles such as succinonitrile and adiponitrile.

Examples of aromatic nitriles include those having an aromatic ring of 4 to 10 carbon atoms, and several typical examples of the aromatic nitriles are the compounds represented by the following general formulae [I]–[VII]

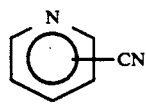
[I]

Those typical thereof are 4-, 3- and 2-cyanopyridines.

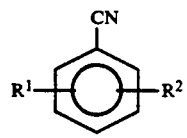
[II]

wherein $R^1$ and $R^2$, respectively, represent H, $CH_3$, OH, $OCH_3$, $OC_2H_5$, Cl, F, CN, $NH_2$ or $NO_2$.

Those typical thereof are benzonitrile, 2-, 3- and 4-chlorobenzonitriles, 2-, 3- and 4-fluorobenzonitriles, 3- and 4-bromobenzonitriles, 3- and 4-nitrobenzonitriles, 3- and 4-aminobenzonitriles 3- and 4-hydroxybenzonitrile, 2-, 3- and 4-tolunitriles, 2-, 3- and 4-methoxybenzonitriles, 3- and 4-ethoxybenzonitriles, phthalonitrile, isophthalonitrile, terephthalonitrile, 2,6-dichlorobenzonitrile, 2,4-dichlorobenzonitrile, 3,5-dichlorobenzonitrile, 2,6-difluorobenzonitrile, and 3,4-difluorobenzonitrile.

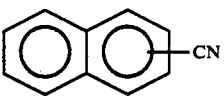
[III]

Those typical thereof are α- and β-naphthonitriles.

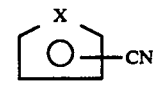
[IV]

wherein X represents S or O.

Those typical thereof are 2-thiophene carbonitrile and 2-furonitrile.

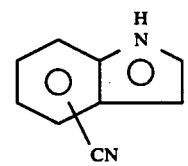
[V]

The typical example thereof is 5-cyanoindole.

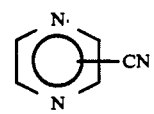
[VI]

The typical example thereof is cyanopyrazine.

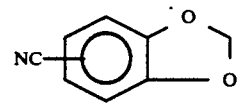
[VII]

The typical example thereof is pyperonylonitrile.

Application of the nitrilase enzyme referred to above upon these nitrile compounds as its substrates will produce the corresponding acids almost without formation of the corresponding amide compounds and thus in almost 100% mole yield. The organic acids produced will be accumulated in the reaction solution/medium, and the organic acids can thus be recovered therefrom by any suitable methods. For instance, the reaction solution is freed from the microbial cells by, e.g. centrifugation, and is then subjected to ammonia removal by, e.g. a treatment with an acid, and is then subjected to recovery of the organic acids by, e.g. extraction or distillation.

The present invention will now be described in more detail with reference to the following examples which are merely illustrative.

EXAMPLES 1 TO 4

A culture medium comprising 1.5% of glucose, 0.75% of sodium glutamate, 0.05% of monopotassium phosphate, 0.05% of dipotassium phosphate, 0.05% of magnesium sulfate heptahydrate, 0.1% of a yeast extract and 0.5% of ε-caprolactam, pH 7.2, was prepared, and poured into the Sakaguchi flasks of 500 ml in 60 ml each, which were sterilized in an autoclave at 120° C. for 20 minutes.

Each of the microbial strains set forth in Table 1 was inoculated onto the culture medium, and the culturing under shaking was conducted at 28° C. for 48 hours.

Each of the microbial cells was collected from each of the culture by centrifugation, and was washed with 0.85% sodium chloride aqueous solution and then suspended in the same amount as the culture of 0.85% sodium chloride aqueous solution.

Each of the cell suspensions was added in an amount of 0.1 ml to a reaction solution comprising 50 mM acrylonitrile or 1.0 ml of 3-cyanopyridine, 0.5 ml of a 100 mM potassium phosphate buffer pH 7.8 and 0.4 ml of distilled water, and the reaction was conducted at 20° C. for 20 minutes. The reaction was terminated by the addition of 0.2 ml of 1N HCl, and the amount of acrylic acid or nicotinic acid produced was assayed by HPLC wherein the M&S Pack C18 column manufactured by MS Kiki, Inc., Japan was used.

The results obtained are set forth in Table 1.

TABLE 1

| Example No. | Strain used | Acrylic acid (mM) | Nicotinic acid (mM) |
|---|---|---|---|
| 1 | Rh. rhodochrous J-1 FERM BP-1478 | 8.6 | 6.7 |
| 2 | Rh. rhodochrous ATCC 33278 | 7.9 | 5.2 |
| 3 | Rh. sp. NCIB 11215 | 1.6 | 2.7 |
| 4 | Rh. sp. NCIB 11216 | 4.4 | 3.5 |

No acrylamide nor nicotinamide, a possible hydrolysis intermediate, was determined at all.

As a comparison, the same 4 runs except for ε-caprolactam not being used were conducted. No nitrilase activities as shown in Table 1 were determined.

EXAMPLES 5 TO 6

The procedure of Example 1 was followed except for the uses of a lactam, in place of ε-caprolactam, which was γ-butyrolactam or δ-valerolactam and of the culturing time, in place of 48 hours, which was 96 hours.

The results obtained are set forth in Table 2.

TABLE 2

| Example No. | Lactam compound | Acrylic acid (mM) | Nicotinic acid (mM) |
|---|---|---|---|
| 5 | γ-Butyrolactam | 5.3 | 4.0 |
| 6 | δ-Valerolactam | 8.5 | 5.5 |

EXAMPLES 7 TO 13

Rhodococcus rhodochrous J-1 was cultured on the same culture medium as used in Example 1 at 28° C. for 96 hours. The cells obtained were crushed, and the supernatant upon centrifugation of the crushed cells was subjected to dialysis against 10 mM potassium phosphate buffer containing 30 (v/v) % of glycerol, pH 7.0, and was then applied to a DEAE-Sephacel column (Pharmacia), equilibrated with the same buffer. The protein was then eluted with a linear gradient of KCl (0 to 0.6M) in the same buffer thereby to collect the fraction having the nitrilase activity.

The crude nitrilase solution obtained was used to determine its activity against the nitrile compounds set forth in Table 3.

Determination of the activity was conducted by the action at 20° C. for 10 minutes of 0.5 ml of the crude enzyme solution which was diluted with distilled water (upon necessity) upon a reaction solution comprising 1.0 ml of each of 20 mM nitrile compounds set forth in Table 3 and 0.5 ml of a 100 mM potassium phosphate buffer (pH 7.8).

The reaction was terminated by the addition of 0.2 ml of 1N HCl.

The amount of the organic acids produced was determined by HPLC wherein the M&S Pack C18 column manufactured by M&S Kiki Inc. Japan was used.

The results obtained are set forth in Table 3, wherein "1 unit (U)" is defined as the velocity of production of organic acid from the nitrile at the rate of 1 μmole/min.

TABLE 3

| Example No. | Substrate/Nitrile | Acid produced | Specific Activity (U/mg-protein) |
|---|---|---|---|
| 7 | Benzonitrile | Benzoic | 5.3 |
| 8 | 3-Cyanopyridine | Nicotinic | 3.8 |
| 9 | Thiophene-2-acetonitrile | Thiophene-2-acetic | 0.50 |
| 10 | Acrylonitrile | Acrylic | 2.1 |
| 11 | Crotonitrile | Crotonic | 0.69 |
| 12 | Methacrylonitrile | Methacrylic | 0.17 |
| 13 | Propionitrile | Propionic | 0.19 |

EXAMPLE 14

Rhodococcus rhodochrous J-1, FERM BP-1478, was cultured on the same culture medium as used in Example 1 at 28° C. for 96 hours. The cells were harvested from the culture medium by centrifugation, and washed with a 50 mM potassium phosphate buffer (pH 7.8), and the cells were then suspended in the same buffer in the same amount.

Acrylonitrile was added portion-wise to 50 ml of the cell suspension held at 20° C. under agitation so that its concentration was held at a level lower than 200 mM. Acrylic acid was produced and accumulated in the reaction solution almost quantitatively. Production of acrylamide as a by-product was not higher than 0.5% (in terms mole ratio).

In passing, the analysis of the ε-caprolactam in the culture medium after the culturing by means of gas chromatography showed that the content of ε-caprolactam was 4.8 g/liter, which in turn corresponds to the recovery of 96%.

COMPARATIVE EXAMPLES 1 TO 4

A culture medium comprising 1.0% of glycerol, 0.5% of polypeptone, 0.3% of a yeast extract and 0.3% of a malt extract, pH 7.2, was prepared, and poured into the Sakaguchi flasks of 500 ml in 100 ml each, which were sterilized in an autoclave at 120° C. for 20 minutes. To each of the flask was added 100 μl of isovaleronitrile aseptically.

To each of the culture media was inoculated each of the microbial strains set forth in Table 4, and the shaking culturing was conducted at 28° C. for 48 hours.

After the culturing, cell suspensions were prepared as in Examples 1 to 4 and the nitrilase activities were determined. The results obtained were set forth in Table 4.

TABLE 4

| Comp. Example No. | Strain used | Acrylic acid (mM) | Nicotinic acid (mM) |
| --- | --- | --- | --- |
| 1 | Rh. rhodochrous J-1, FERM BP-1478 | 1.84 | 1.34 |
| 2 | Rh. rhodochrous ATCC 33278 | 1.35 | 0.986 |
| 3 | Rh. sp. NCIB 11215 | 0.0865 | 0.146 |
| 4 | Rh. sp. NCIB 11216 | 1.62 | 0.968 |

What is claimed is:

1. In a process for preparing an organic acid which comprises converting a nitrile compound by the action thereupon of a nitrilase enzyme inherent in a microorganism into the corresponding organic acid, the improved process comprising converting the nitrile into the corresponding acid by the action of a nitrilase enzyme obtained by culturing a microbial strain of Rhodococcus selected from the group consisting of *Rhodococcus rhodochrous* J-1 Ferm BP-1478, *Rhodococcus rhodochrous* ATCC 33278, Rhodococcus sp. NCIB 11215 and Rhodococcus sp. NCIB 11216 in the presence of a lactam compound contained in the range of 0.05 to 2.0 w/v in the culture medium in which the strain of Rhodococcus is cultured.

2. The process as claimed in claim 1, wherein the *Rhodococcus rhodochrous* is selected from the group consisting of *Rh. rhodochrous*J-1, FERM BP-1478 and *Rh. rhodochrous* ATCC 33278.

3. The process as claimed in claim 2, wherein the *Rhodococcus rhodochrous* is *Rh. rhodochrous* J-1, FERM BP-1478.

4. The process as claimed in claim 1, wherein the Rhodococcus is selected from the group consisting of Rhodococcus sp. NCIB 11215 and Rhodococcus sp. NCIB 11216.

5. The process as claimed in claim 1, wherein the lactam compound is selected from the group of cyclic intramolecular amides of 4 to 6 carbon atoms.

6. The process as claimed in claim 1 wherein the nitrile compound is selected from the group consisting of aliphatic and aromatic mononitriles and dinitriles.

7. The process as claimed in claim 1, wherein the nitrile compound is selected from the group consisting of aliphatic mononitrile and dinitrile having 2 to 6 carbon atoms.

8. The process as claimed in claim 7, wherein the nitrile compound is acrylonitrile.

9. The process as claimed in claim 1, wherein the nitrile compound is selected from the group consisting of aromatic mononitrile and dinitrile having 4 to 10 carbon atoms in its aromatic nucleus.

10. The process as claimed in claim 9, wherein the nitrile compound is an aromatic nitrile selected from the group consisting of:

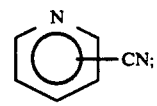
I

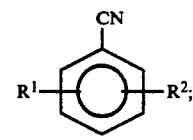
II wherein $R^1$ and $R^2$, respectively, represent H, $CH_3$, OH, $OCH_3$, $OC_2H_5$, Cl, F, CN, $NH_2$, or $NO_2$;

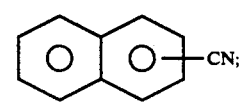
III

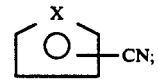
IV wherein X represents S or O;

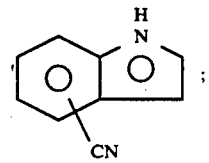
V

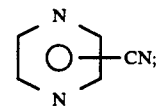
VI and

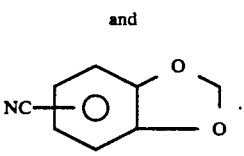
VII

11. The process as claimed in claim 10, wherein the aromatic nitrile is a cyanopyridine of the formula.

12. The process as claimed in claim 1, wherein the nitrile compound is a mononitrile.

13. The process as claimed in claim 1, wherein the nitrile is an aliphatic nitrile.

14. The process as claimed in claim 1, wherein the nitrile is an aliphatic mononitrile.

15. The process as claimed in claim 1, wherein the nitrile is an aliphatic mononitrile having 2-6 carbon atoms.

* * * * *